United States Patent [19]
Dahl

[11] Patent Number: 5,017,103
[45] Date of Patent: May 21, 1991

[54] CENTRIFUGAL BLOOD PUMP AND MAGNETIC COUPLING

[75] Inventor: Terrance J. Dahl, Salt Lake City, Utah

[73] Assignee: St. Jude Medical, Inc., St. Paul, Minn.

[21] Appl. No.: 320,212

[22] Filed: Mar. 6, 1989

[51] Int. Cl.$^5$ .................... F04D 29/00; F04D 29/12
[52] U.S. Cl. .................... 417/420; 417/423.7
[58] Field of Search ............ 417/423.7, 420; 415/98, 415/229; 416/181, 184; 384/610; 464/29

[56] References Cited

U.S. PATENT DOCUMENTS

| | | | |
|---|---|---|---|
| 851,457 | 4/1907 | Verner. | |
| 1,225,805 | 5/1917 | Griepe. | |
| 1,880,911 | 10/1932 | Durdin. | |
| 2,028,360 | 1/1936 | Srink. | |
| 2,154,199 | 4/1939 | Colwell et al. | 286/7 |
| 2,157,597 | 5/1939 | Dupree | 308/36.2 |
| 2,207,371 | 7/1940 | Blackmore et al. | 288/2 |
| 2,231,690 | 2/1941 | Sheldrick et al. | 286/7 |
| 2,243,227 | 5/1941 | Stratton et al. | 286/7 |
| 2,471,753 | 5/1949 | Johnston. | |
| 2,481,172 | 9/1949 | Staggs. | |
| 2,540,968 | 2/1951 | Thomas | 308/15 |
| 2,669,668 | 2/1954 | Okulitch et al. | 310/104 |
| 2,810,349 | 10/1957 | Zozulin. | |
| 3,074,347 | 1/1963 | Clymer | 417/420 |
| 3,299,819 | 1/1967 | McCoy. | |
| 3,487,784 | 1/1970 | Rafferty et al. | |
| 3,541,607 | 11/1970 | Greene | 415/112 |
| 3,608,088 | 9/1971 | Dorman et al. | 3/1 |
| 3,647,324 | 3/1972 | Rafferty et al. | 417/420 |
| 3,867,655 | 2/1975 | Stengel et al. | 310/66 |
| 3,941,517 | 3/1976 | Miyahara | 417/420 |
| 3,957,389 | 5/1976 | Rafferty et al. | 415/1 |
| 3,970,408 | 7/1976 | Rafferty et al. | 415/60 |
| 4,037,984 | 7/1977 | Rafferty et al. | 415/60 |
| 4,065,234 | 12/1977 | Yashiyuki et al. | 417/420 |
| 4,115,040 | 9/1978 | Knorr | 417/420 |
| 4,135,253 | 1/1979 | Relch et al. | 3/1 |
| 4,253,798 | 3/1981 | Sugiura | 415/98 |
| 4,304,532 | 12/1981 | McCoy | 417/420 |
| 4,589,822 | 5/1986 | Clausen et al. | 415/170 |
| 4,606,698 | 8/1986 | Clausen et al. | 415/170 |
| 4,643,641 | 2/1987 | Clausen et al. | 415/170 |
| 4,645,432 | 2/1987 | Tata | 417/420 |
| 4,678,409 | 7/1987 | Kurokawa | 417/420 |
| 4,688,998 | 8/1987 | Olsen et al. | 417/356 |
| 4,844,707 | 7/1989 | Kletschka | 417/420 |

FOREIGN PATENT DOCUMENTS 1051123 2/1959 Fed. Rep. of Germany.
43-17206 7/1943 Japan.

Primary Examiner—Leonard E. Smith
Assistant Examiner—David W. Scheuermann
Attorney, Agent, or Firm—Spensley, Horn, Jubas & Lubitz

[57] ABSTRACT

A centrifugal blood pump having a pumping chamber provided with an axial inlet and a circumferential outlet and provided with a rotatable impeller having a plurality of radially extending blood propelling vanes. The vanes are configured to each have a blade angle which varies monotonically toward the periphery of the chamber. The pumping chamber is delimited by an impeller housing provided with an opening through which the impeller shaft extends into the chamber, the opening having an outline which conforms closely to the outline of the shaft, and the pump further includes a bearing housing secured to the impeller housing and delimiting a bearing chamber into which the shaft extends; bearings disposed in the bearing chamber and rotatably supporting the shaft; and a seal located in the bearing chamber adjacent the opening and surrounding the shaft to form a fluid seal between the blood pumping chamber and the bearing chamber. The impeller is driven by a plurality of magnetizable plates secured to the impeller and spaced apart about the longitudinal axis, and a rotatable magnetic drive assembly disposed outside of the impeller housing and mounted for rotation about the longitudinal axis, the drive assembly producing a magnetic field which passes through each plate for attracting the plates to the drive assembly and rotating the impeller with the drive assembly.

26 Claims, 2 Drawing Sheets

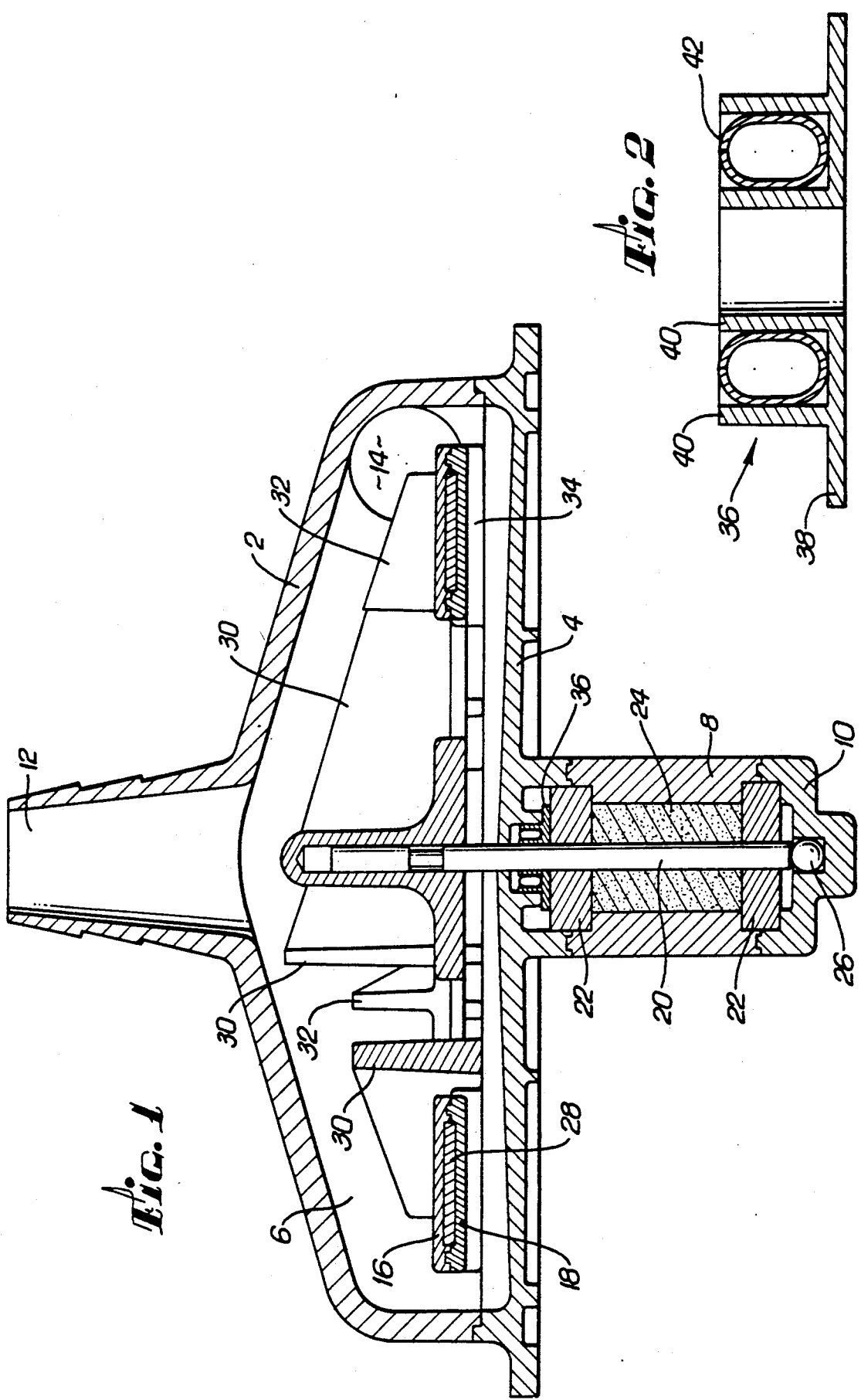

CENTRIFUGAL BLOOD PUMP AND MAGNETIC COUPLING

BACKGROUND OF THE INVENTION

The present invention relates to centrifugal blood pumps intended for extracorporeal pumping of blood.

Known blood pumps of this type have been found to be less than totally reliable, due at least in part to their mechanical complexity and to the use of configurations which permit blood thrombus formation.

SUMMARY OF THE INVENTION

It is a primary object of the present invention to provide a novel centrifugal blood pump which reduces the danger of blood hemolysis and thrombus formation.

Another object of the invention is to provide a novel centrifugal blood pump which is structurally simpler than existing pumps of this type, and hence operates more reliably.

The above and other objects are achieved, according to the present invention, in a centrifugal blood pump composed of an impeller housing having a generally circular cross section and a longitudinal axis and delimiting a blood pumping chamber having a blood inlet port extending along the longitudinal axis and a blood outlet port located at the periphery of the chamber, an impeller provided with a plurality of radially extending vanes disposed in the chamber, a shaft supporting the impeller for rotation about the longitudinal axis of the blood pumping chamber, and magnetic drive means for rotating the impeller in a sense to cause the vanes to propel blood from the inlet port to the outlet port, by the improvement wherein the vanes are configured to each have a blade angle which varies monotonically toward the periphery of the chamber.

The objects of the present invention are further achieved by other novel features of the impeller, by a novel magnetic drive system, and by a novel sealing arrangement for the impeller shaft, all of which will be described in detail below.

With regard to a primary aspect of the invention, applicants have concluded that, in pumps of the type under consideration, blood hemolysis is caused by mechanical stresses imposed on the blood by the pumping process and have conceived and developed a novel impeller configuration which acts on the blood in such a manner as to significantly reduce the occurrence of hemolysis. Basically, impellers according to the present invention are constructed to subject blood as it enters and flows through the pump to smooth velocity transitions and to reduce cavitation in the pump, particularly at the inlet.

Applicants have determined that this objective can be achieved by giving the impeller vanes a blade angle which varies from the end associated with the pump inlet and to the end associated with the pump outlet such that the tangent of the blade angle increases, as a function of radial distance from the impeller axis. It is presently believed that an optimum result will be achieved if the tangent increases linearly, or at least approximately linearly, from the inlet to the outlet.

BRIEF DESCRIPTION OF THE DRAWINGS

FIG. 1 is a cross-sectional, elevational view of a preferred embodiment of a centrifugal blood pump according to the present invention.

FIG. 2 is a cross-sectional, elevational view of one element provided in the pump of FIG. 1.

DESCRIPTION OF THE PREFERRED EMBODIMENTS

Figure 4:
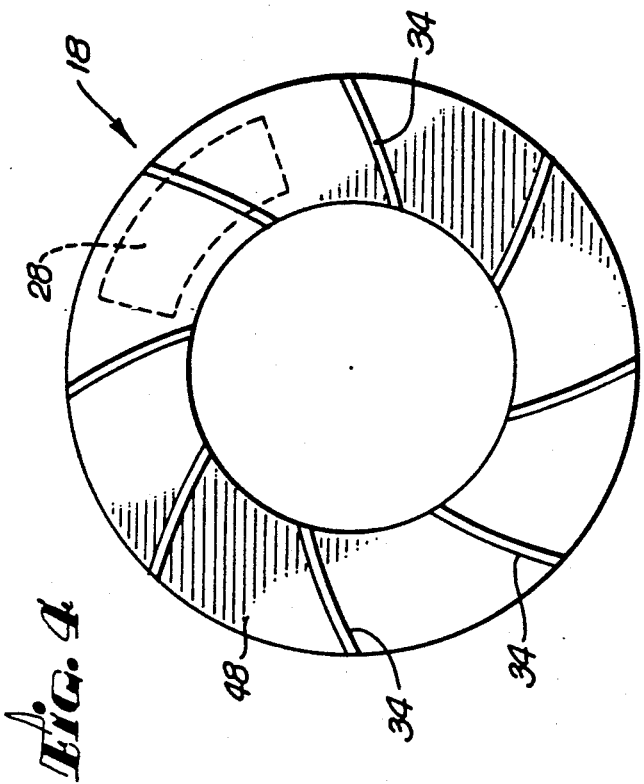
FIG. 4 is a bottom plan view of the second impeller element of the pump shown in FIG. 1.

One embodiment of a centrifugal blood pump according to the present invention is illustrated in FIG. 1, which is a cross-sectional view taken along a plane passing through the axis of rotation of the pump impeller.

The illustrated pump includes a housing composed of a forward housing part 2 and a rear housing part 4, parts 2 and 4 together enclosing a pump chamber 6. The pump housing further includes a bearing housing 8 and a bearing cap 10, with the rear end of housing 8 being closed by cap 10 and the forward end of housing 8 being closed by rear housing part 4.

Forward housing part 2 is formed to have an inlet passage 12 which extends along the pump axis and an outlet passage 14 which extends in a generally tangential direction at the periphery of chamber 6.

Within chamber 6 there is mounted an impeller which, according to the present invention, is formed of a forward impeller part 16 and a rear impeller part 18, parts 16 and 18 being joined and bonded together along a plane perpendicular to the pump axis. Impeller 16, 18 is mounted on an impeller shaft 20 which is rotatably supported by a pair of journal bearings 22 secured in bearing housing 8. The region within housing 8 between bearings 22 is preferably filled with a mass 24 of a suitable grease.

The interior surface of cap 10 is provided with a cylindrical blind bore containing a steel ball 26 which constitutes a thrust bearing providing axial support for shaft 20 and impeller 16, 18.

Between rear housing part 4 and the journal bearing 22 adjacent thereto there is disposed a shaft seal 36, which will be described in detail below.

Impeller parts 16 and 18 are formed to delimit a plurality of circumferentially spaced, arcuate chambers, six such chambers being provided in one practical embodiment of the invention. Each chamber holds an arcuate drive plate 28 made of a magnetically permeable, but unmagnetized, material. Plates 28 can be made relatively thin, a thickness of the order of 0.040" having been found to be suitable.

Forward impeller part 16 carries a plurality of circumferentially spaced long vanes 30 and a plurality of circumferentially spaced short vanes 32 interposed circumferentially between successive long vanes 30. All vanes 30 and 32 project axially toward inlet passage 12 and the edges of vanes 30 and 32 which face toward inlet passage 12 conform generally to the outline of forward housing part 2.

Rear impeller part 18 carries a plurality of short vanes 34 each of which is aligned with and corresponds in configuration to a respective one of short vanes 32 and the outer portions of long vanes 30. The portion of each long vane 30 which is radially enclosed by a respective vane 34 extends axially toward rear housing part 4 to the same level as the associated vane 34 so that, at the side facing rear housing part 4, the respective vane 34 forms a radial continuation of the associated vane 30.

Impeller shaft 20 enters chamber 6 via a passage provided in rear housing part 4, which passage is dimensioned to provide the minimum permissible clearance for shaft 20. Preferably, a radial clearance of no more than 0.001 to 0.002" is provided.

Moreover, the edge of the shaft passage which borders chamber 6 is formed to be sharp so as to constitute a shear edge.

The passage for shaft 20 is isolated from the interior of bearing chamber 8 by shaft seal 36.

As shown in FIG. 2, shaft seal 36 is composed of an annular flange portion 38 which will bear against the journal bearing 22 which is adjacent rear housing part 4. Shaft seal 36 further includes two concentric, radially spaced cylindrical portions 40, the outer one of which bears against the surface of a cylindrical relief opening provided in rear housing part 4. Inner cylindrical portion 40 is dimensioned to establish a close fit with shaft 20.

Between cylindrical portions 40 there is interposed a pressure member 42 composed of a spiral spring bent into a toroidal form and made of a suitable material, such as stainless spring steel. Member 42 is configured to apply a radial pressure to cylindrical portions 40, thereby pressing those portions against shaft 20 and the inner surface of the cylindrical relief opening provided in rear housing part 4, respectively. Thus, an effective seal is provided between chamber 6 and the interior of bearing housing 8.

As a result of the close fit between shaft 20 and the opening in rear housing part 4, shaft seal 36 is, in effect, "hidden" from chamber 6. This helps to prevent thrombus formation on seal 36.

The supporting of shaft 20 by journal bearings 22, instead of ball-type bearings, and the elimination of air from the bearing chamber by filling it with mass 24 of grease, are major contributing factors to the superior reliability of pumps according to the present invention. With this arrangement, seal 36 is not required to effect a perfect sealing action but need only prevent gross migration of blood and grease.

Figure 3:
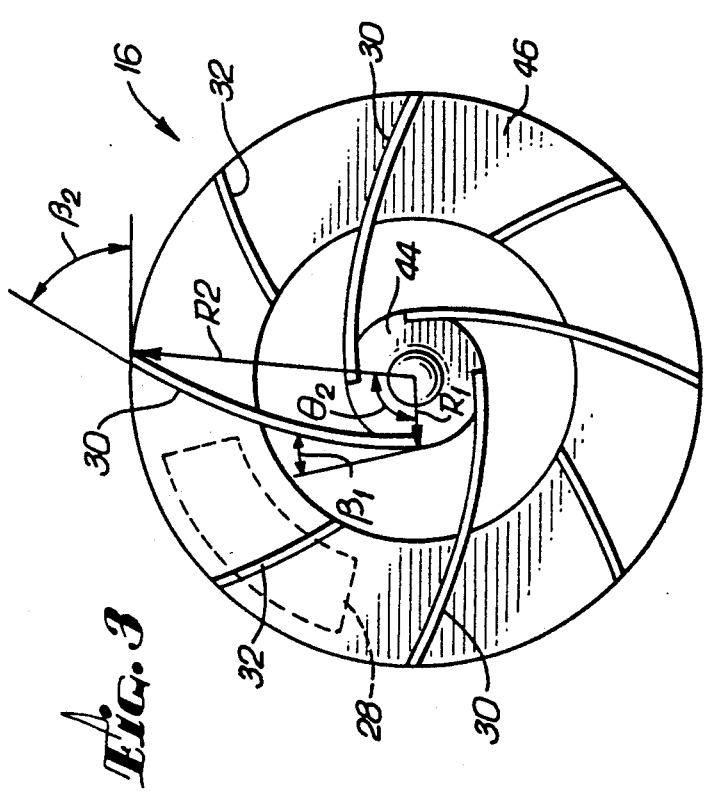
FIG. 3 is a top plan view of one impeller component of the pump of FIG. 1.

FIG. 3 is a plan view, looking in the direction of fluid flow into the pump, of forward impeller part 16, which is basically composed of an inner hub portion 44 and an outer annular portion 46, the two portions being secured together by means of long vanes 30. Short vanes 32 are interposed between long vanes 30 so that vanes 30 and 32 are equispaced about the circumference of upper impeller part 16.

FIG. 4 is a plan view of rear impeller part 18, looking opposite to the direction of fluid flow into the pump, i.e., opposite to the direction of the view of FIG. 3. Rear impeller part 18 is composed essentially of an annular ring 48 carrying short vanes 34, each of which is aligned with an associated portion of a respective one of vanes 30 or 32.

According to preferred embodiments of the invention, each vane 30, 32, 34 is given a curvature such that the variation of the tangent of the blade angle as a function of impeller radius has a positive value along the length of each blade.

FIGS. 3 and 4 additionally illustrate one of the drive plates 28 which is installed between impeller parts 16 and 18 and which are spaced apart around the circumference of the impeller.

As regards the axial spacing between vanes 30, 32, 34 and housing parts 2 and 4, these selected to be small enough to achieve a satisfactory pumping force, and yet large enough to minimize the shear forces imposed on the blood. On the basis of these considerations, in one exemplary embodiment of the invention, the axial spacing between vanes 30 and 34 and rear housing part 4 is of the order of 0.12 inch at the outer diameter of the impeller. In this embodiment, which is illustrated in FIG. 1, the surface of rear housing part 4 which delimits chamber 6 has a slight upward slope toward shaft 20 so that the axial spacing between the vanes and that surface of lower housing part 4 exhibits a slight progressive decrease in the direction toward shaft 20. This axial spacing dimension was provided in a pump whose impeller vanes are configured so that the inner end of each vane 30 is at a distance of 0.3 inch from the axis of rotation of shaft 20 and the outer end of each vane is at a distance of 1.4 inches from the axis of rotation of shaft 20. In fact, FIG. 1 is drawn to scale and represents a pump having the above-stated dimensions.

Vanes 34 and the portions of vanes 30 which project toward rear housing part 4 act to subject blood which is present between the impeller and rear housing part 4 to a radial outward force, and thereby prevent blood from recirculating around the outer edge of the impeller. Thus, the action of these vane portions together with the sharp shear edge provided by rear housing part 4 around shaft 20 at the side bordering chamber 6 serve to sweep blood away from the region where shaft 20 passes through rear housing part 4, which is a potential area of stasis, and thus prevent thrombus formation at that location.

As noted earlier herein, vanes 30, 32, 34 are configured with the goal of minimizing the acceleration and shock experienced by blood within the pump. Preferably, the inlet blade angle of each vane, the blade angle being, at any point along a blade, the angle between the blade surface and a circle centered on the axis of impeller rotation and passing through the point in question, is selected so that, for a selected impeller speed, the velocity produced by each vane closely corresponds to the inlet flow velocity of the blood.

According to a preferred embodiment of the invention, the configuration of each vane 30, 32, 34 was determined on the basis of the following equation:

$$R = R_1 + C_1 \cdot \Theta + C_2 \cdot \Theta^{C_3} \qquad (1)$$

where:
R is the radial distance from each point along the vane to the axis of rotation of shaft 20;
$R_1$ is the radial distance from the end of each long vane 30 closest of the axis of shaft rotation to that axis, i.e., at the inlet end of each long vane 30;
$\Theta$ is the angle, in radians, about the axis of rotation of shaft 20, between a line extending between that axis and the inlet end of a long vane 30 and a line extending between that axis and the point on the same vane whose radial distance from the axis is R;
$C_1 = R_1 \cdot \tan\beta_1$, where $\beta_1$ is the blade angle in radians, of a vane 30 at its inlet end;
$C_2 = (R_2 \tan\beta_2 - C_1)/(C_3 \cdot \Theta_2(C_3 - 1))$,
where $R_2$ is the radial distance from the end of each vane furthest from the axis of rotation of shaft 20 to that axis, $\beta_2$ is the blade angle, in radians, of each vane at the end furthest from the axis of rotation of shaft 20, and $\Theta_2$ is the value for Θ associated with the radial distance R2; and $C3 = (R2 \cdot \tan\beta_2 - C1) \cdot \Theta_2 / (R_2 - R_1 - C1 \cdot \Theta_2)$, with the following selected parameters being used: R1=0.3"; R₂=1.4"; β₁=0.1745 Rad=10°; β₂=1.047 Rad=60°; and Θ₂=2.094 Rad=120°.

R1, R2, $\beta_1$, $\beta_2$ and $\Theta_2$ are shown in FIG. 3. Blade angle, Θ, is the angle, at a point along a vane, between a line tangent to the blade surface and a line tangent to a circle passing through that point and centered on the axis of rotation of shaft 20.

Figure 5:
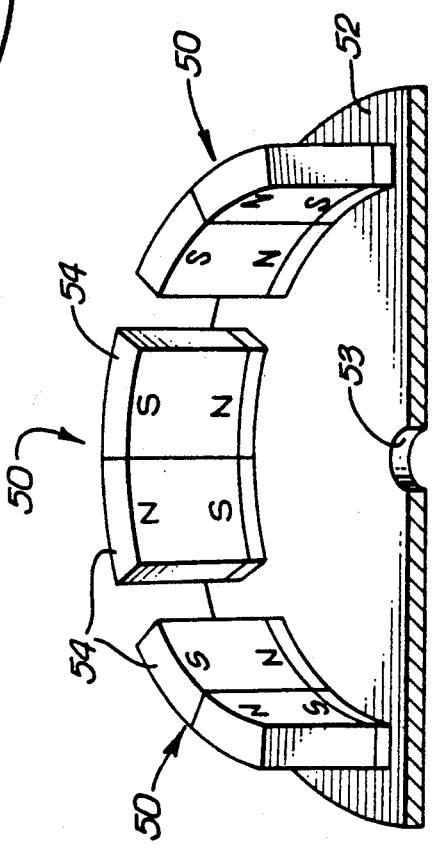
FIG. 5 is a cutaway perspective view of a portion of a magnetic drive system for the pump of FIG. 1.

FIG. 5 illustrates the basic components of a magnetic drive according to the present invention. This drive is composed of a plurality of permanent magnet units 50 mounted on a plate 52 having a central opening 53 for connection to the shaft of a drive motor. One-half of the drive is shown in FIG. 5. Each magnet unit 50 is composed of two bar magnets 54 each having its magnetic axis oriented parallel to the axis of rotation of plate 52, with the magnets 54 of each unit 50 being oriented in polarity opposition to one another, as shown. Moreover, the magnetic poles of each unit 50 are oriented opposite to those of each adjacent unit 50. Each unit 50 is further composed of an arcuate plate 56 of ferromagnetic material completing the magnetic circuit at one end of the associated unit 50.

The magnetic drive is disposed directly beneath rear housing part 4 so that magnet units 50 surround housing 8 and plate 52 is behind cap 10. Thus, the end of each magnet unit 50 which is remote from plate 52 faces a respective one of plates 28. The spacing between plates 28 and units 50 is made as small as possible in order to minimize the air gap between each plate 28 and its associated unit 50, and thus maximize the magnetic attraction exerted on each plate 28.

The arrangement of magnetic units 50 is such that the magnetic flux path of each unit is completed through a respective one of plates 28 and the magnetic paths associated with adjacent ones of plates 28 are maintained isolated from each other by the orientations of the magnets associated with adjacent units 50. Thus, as plate 52 is rotated, the magnetic attraction forces exerted on plates 28 cause impeller 16, 18 to rotate in unison therewith.

In addition, the magnetic attraction exerted by units 50 pulls impeller 16, 18 downwardly in order to press shaft 20 against ball 26.

The drive arrangement shown in FIG. 5 produces particularly strong magnetic forces, making possible the use of thin, unmagnetized plates 28 and permitting a sufficient drive force to be imparted to impeller 16, 18 even with a comparatively large air gap between units 50 and plates 28.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In a centrifugal blood pump composed of an impeller housing having a generally circular cross section and a longitudinal axis and delimiting a blood pumping chamber having a blood inlet port extending along the longitudinal axis and a blood outlet port located at the periphery of the chamber, an impeller provided with a plurality of radially extending curved vanes disposed in the chamber, each said vane having a first end adjacent said blood inlet port and a second end extending toward the periphery of the chamber, an axial shaft supporting the impeller for rotation about the longitudinal axis of the blood pumping chamber, and drive means for rotating the impeller in a sense to cause the vanes to propel blood radially from the inlet port to the outlet port, the improvement wherein said vanes are configured according to the formula:

$$R = R1 + C1 \cdot \Theta + C2 \cdot \Theta^{C3}$$

where:
R is the radial distance from each point along each vane to the axis of rotation of said shaft;
R1 is the radial distance from the first end of each vane to the axis of said shaft;
Θ is the angle, in radians, about the axis of rotation of the shaft, between a line extending between the shaft axis on the first end of each vane and a line extending between the shaft axis and the point on the same vane whose radial distance from the shaft axis is R;
$C1 = R1 \cdot \tan B_1$, where B is the angle, at a point along a vane, between a line tangent to the blade surface and a line tangent to a circle passing through that point and centered on the axis of said shaft, $B_1$ is the blade angle in radians, of each vane at its first end;
$C2 = (R_2 \tan B_2 - C1)/(C3 \cdot \Theta_2(C3 - 1))$, where R 2 is the radial distance from the second end of each vane to the shaft axis, $B_2$ is the blade angle, in radians, of each vane at the second end, and $\Theta_2$ is the value for Θ associated with the radial distance R2; and wherein
$C3 = (R2 \cdot \tan B_2 - C1) \cdot \Theta_2 / (R_2 - R_1 - C1 \cdot \Theta_2)$.

2. A pump as defined in claim 1 wherein said vanes are curved such that during rotation of said impeller at a selected speed, the magnitude of the velocity imparted to blood by the first end of said valve is substantially equal to the speed of blood flowing through said inlet port.

3. A pump as defined in claim 2 wherein said impeller comprises a planar support plate and said vanes project in both axial directions from said plate.

4. A pump as defined in claim 3 wherein said support plate is provided with an annular opening adjacent the second ends of said vanes for passage of blood axially from one side of the other of said support plate.

5. A pump as defined in claim 1 wherein:
R1=0.3"; R₂=1.4"; $B_1$=0.1745 Rad=10°;
$B_2$=1.047 Rad=60°; and
$\Theta_2$=2.094 Rad=120°.

6. A pump as defined in claim 1 wherein said impeller housing is provided with an opening through which said shaft extends into said chamber, said opening having an outline which conforms closely to the outline of said shaft, and further comprising: a bearing housing secured to said impeller housing and delimiting a bearing chamber into which said shaft extends; bearing means disposed in said bearing chamber and rotatably supporting said shaft; and seal means located in said bearing chamber adjacent said opening and surrounding said shaft to form a fluid seal between said blood pumping chamber and said bearing chamber.

7. A pump as defined in claim 6 wherein the end of said opening which borders said chamber is formed to have a distinct edge.

8. A pump as defined in claim 6 wherein said bearing means comprise two journal bearings spaced apart along said longitudinal axis, and further comprising a mass of lubricating grease filling the region of said bearing chamber between said journal bearings.

9. A pump as defined in claim 6 further comprising a thrust bearing disposed in said bearing chamber and providing axial support for said shaft.

10. A pump as defined in claim 9 wherein said thrust bearing is constituted by a metal ball.

11. A pump as defined in claim 6 wherein said opening is dimensioned such that the difference between the radius of said opening and the radius of said shaft is not greater than 0.002 inch.

12. In a centrifugal blood pump composed of an impeller housing having a generally circular cross section and a longitudinal axis and delimiting a blood pumping chamber having a blood inlet port extending along the longitudinal axis and a blood outlet port located at the periphery of the chamber, an impeller provided with a plurality of radially extending vanes disposed in the chamber, a shaft supporting the impeller for rotation about the longitudinal axis of the blood pumping chamber, and drive means for rotating the impeller in a sense to cause the vanes to propel blood radially from the inlet port to the outlet port, the improvement wherein said drive means comprise: a plurality of magnetizable plates secured to said impeller and spaced apart about the longitudinal axis; and a rotatable magnetic drive assembly disposed outside of said impeller housing and mounted for rotation about the longitudinal axis, said drive assembly comprising means producing a magnetic field which passes through each said plate for attracting said plates to said drive assembly and rotating said impeller with said drive assembly.

13. A pump as defined in claim 12 wherein said means producing a magnetic field are constructed to produce a separate magnetic field for each said plate.

14. A pump as defined in claim 13 wherein said means producing a magnetic field comprise a plurality of magnet units, each magnet unit being associated with a respective plate and comprising two bar magnets having their magnetic axes oriented parallel to the longitudinal axis and in polarity opposition to one another, and a ferromagnetic plate extending between said two bar magnets at the ends thereof remote from said impeller housing.

15. A pump as defined in claim 14 wherein the magnetic axis of each bar magnet is oriented to have the same polarity as the magnetic axis of the adjacent bar magnet of the adjacent magnet unit such that the magnetic field produced by each said magnet unit is circumferentially repelled by the magnetic fields of the respectively adjacent magnet units.

16. In a centrifugal blood pump composed of an impeller housing having a generally circular cross section and a longitudinal axis and delimiting a blood pumping chamber having a blood inlet port extending along the longitudinal axis and a blood outlet port located at the periphery of the chamber, an impeller provided with a plurality of radially extending vanes disposed in the chamber, a shaft supporting the impeller for rotation about the longitudinal axis of the blood pumping chamber, and drive means for rotating the impeller in a sense to cause the vanes to propel blood radially from the inlet port to the outlet port, the improvement wherein said impeller housing is provided with an opening through which said shaft extends into said chamber, said opening having an outline which conforms closely to the outline of said shaft, a plurality of magnetizable plates secured to said impeller and spaced apart about the longitudinal axis, and said pump further comprises: a bearing housing secured to said impeller housing and delimiting a bearing chamber into which said shaft extends; sleeve bearing means disposed in said bearing chamber and rotatably supporting said shaft; and seal means located in said bearing chamber adjacent said opening and surrounding said shaft to form a fluid seal between said blood pumping chamber and said bearing chamber.

17. A pump as defined in claim 16 wherein the end of said opening which borders said chamber is formed to have a distinct edge.

18. A pump as defined in claim 16 wherein said bearing means comprise two journal bearings spaced apart along said longitudinal axis, and further comprising a mass of lubricating grease filling the region of said bearing chamber between said journal bearings.

19. A pump as defined in claim 16 further comprising a thrust bearing disposed in said bearing chamber and providing axial support for said shaft.

20. A pump as defined in claim 19 wherein said thrust bearing is constituted by a metal ball.

21. A pump as defined in claim 16 wherein said opening is dimensioned such that the difference between the radius of said opening and the radius of said shaft is not greater than 0.002 inch.

22. In a centrifugal blood pump composed of an impeller housing having a generally circular cross section and a longitudinal axis and delimiting a blood pumping chamber having a blood inlet port extending along the longitudinal axis and a blood outlet port located at the periphery of the chamber, an impeller provided with a plurality of radially extending vanes disposed in the chamber, a shaft supporting the impeller for rotation about the longitudinal axis of the blood pumping chamber, and drive means for rotating the impeller in a sense to cause the vanes to propel blood radially from the inlet port to the outlet port, the improvement wherein said drive means comprise: a plurality of magnetizable plates secured to said impeller and spaced apart about the longitudinal axis; and a rotatable magnetic drive assembly disposed outside of said impeller housing and mounted for rotation about the longitudinal axis, said drive assembly comprising means producing a magnetic field which passes through each said plate for attracting said plates to said drive assembly and rotating said impeller with said drive assembly.

23. A pump as defined in claim 22 wherein said means producing a magnetic field are constructed to produce a separate magnetic field for each said plate.

24. A pump as defined in claim 23 wherein said means producing a magnetic field comprise a plurality of magnet units, each magnet unit being associated with a respective plate and comprising two bar magnets having their magnetic axes oriented parallel to the longitudinal axis and in polarity opposition to one another, and a ferromagnetic plate extending between said two bar magnets at the ends thereof remote from said impeller housing.

25. A pump as defined in claim 24 wherein the magnetic axis of each bar magnet is oriented to have the same polarity as the magnetic axis of the adjacent bar magnet of the adjacent magnet unit such that the magnetic field produced by each said magnet unit is circumferentially repelled by the magnetic fields of the respectively adjacent magnet units.

26. In a centrifugal blood pump composed of an impeller housing having a longitudinal axis and delimiting a blood pumping chamber having a blood inlet port and a blood outlet port, an impeller provided with a plurality of vanes disposed in the chamber, a shaft supporting the impeller for rotation about the longitudinal axis of the blood pumping chamber, and drive means for rotating the impeller in a sense to cause the vanes to propel blood from the inlet port to the outlet port, the improvement wherein said drive means comprise: a plurality of magnetizable plates secured to said impeller and spaced apart about the longitudinal axis; and a rotatable magnetic drive assembly disposed outside of said impeller housing and mounted for rotation about the longitudinal axis, said drive assembly comprising means producing a magnetic field which passes through each said plate for attracting said plates to said drive assembly and rotating said impeller with said drive assembly.

* * * * *